United States Patent [19]

Charney et al.

[11] 4,427,029
[45] Jan. 24, 1984

[54] PULSE DAMPER FOR CHROMOATOGRAPHY SYSTEMS

[75] Inventors: Andrew R. Charney, State College; Paul W. Kercher, Pennsylvania Furnace; Stanley A. Stone, State College, all of Pa.

[73] Assignee: Scientific Systems, Inc., State College, Pa.

[21] Appl. No.: 440,810

[22] Filed: Nov. 12, 1982

[51] Int. Cl.³ ............................................. F16L 55/04
[52] U.S. Cl. .................................... 138/30; 210/198.2
[58] Field of Search .................. 138/30, 26; 220/85 B; 417/540, 542, 543; 277/223; 210/198.2; 73/707

[56] References Cited

U.S. PATENT DOCUMENTS

| | | | |
|---|---|---|---|
| 3,333,604 | 8/1967 | Birdwell | 138/30 |
| 3,608,911 | 9/1971 | Prasse et al. | 277/223 X |
| 3,984,315 | 10/1976 | Ernst et al. | 210/31 C |
| 4,024,061 | 5/1977 | Gatiss | 417/540 X |
| 4,163,461 | 8/1979 | Jacobellis | 138/30 |
| 4,186,776 | 2/1980 | Burton | 138/30 |
| 4,222,414 | 9/1980 | Achener | 138/30 |
| 4,383,551 | 5/1983 | Lynch | 137/593 |

FOREIGN PATENT DOCUMENTS

| | | | |
|---|---|---|---|
| 2623950 | 1/1977 | Fed. Rep. of Germany | 138/30 |
| 1149443 | 12/1957 | France | 138/30 |

*Primary Examiner*—Stephen Marcus
*Assistant Examiner*—Mark Thronson
*Attorney, Agent, or Firm*—C. Hercus Just

[57] ABSTRACT

A pulse damper for inclusion in chromatograhy systems subjected to high pressures and comprising a body having one face from which a cavity extends inwardly to receive non-aqueous compressible fluid, a non-metallic diaphragm of limited flexibility extending across said cavity and clamped to the rim thereof by a cover having spaced ports respectively for inlet and outlet of a liquid vehicle for material being analyzed, said cover having in the face thereof which is adjacent the diaphragm a circular groove communicating with said ports to transmit therebetween the liquid being processed, and ports in the walls of the body which define the cavity respectively communicating with a pressure-indicating gauge and serving as a filling opening closed by a plug.

7 Claims, 5 Drawing Figures

PULSE DAMPER FOR CHROMOATOGRAPHY SYSTEMS

BACKGROUND OF THE INVENTION

The present invention pertains to the practice of high pressure liquid chromatography in which a chromatographic column is connected by suitable conduit to a reciprocating type pump operable to transmit a liquid vehicle from a supply reservoir, through a pulse damper which embodies the present invention, the liquid then being carried to an injection valve where a liquid sample to be processed is entrained in the liquid vehicle, following which said sample is transmitted through the column for determination of the constituents of the sample being processed. The liquid vehicle usually is a suitable chemical solvent which is non-reactive with the sample which is entrained therein and neither the liquid vehicle or sample are chemically reactive with the material with which the test column is packed in accordance with the usual practice of chromatography.

In such systems, the solvent flow paths should have minimum internal volume and be well swept so as to afford continuous movement of the liquid solvent and test material through the system and is important in solvent changeover and when using gradient chromatography techniques. If excessive internal volume exists, it tends to cause mixing which is detrimental to efficient solvent changeover and causes loss of predictable time-based solvent proportions in gradient work.

Various types of pulse dampers have been developed heretofore for certain purposes. For example, prior U.S. Pat. No. 3,333,604, to Birdwell, dated Aug. 1, 1967, discloses a pulsation reducer primarily adapted for use with car washing equipment in which relatively high pressure fluid systems are desired. A pair of disks which are slightly concave are bolted together to clamp a flexible diaphragm adjacent one side of a cavity, one of the disks having openings therein for application of fluid under pressure against one face of the diaphragm and pneumatic pressure is provided in the cavity to react against the diaphragm and absorb pulsations imposed upon the same by fluid being pumped by a reciprocating type pump.

One example of a chromatography system in which a pulse damper is included forms the subject matter of prior U.S. Pat. No. 3,984,315, to Ernst et al, dated Oct. 5, 1976, and in which the chromatographic column is in circuit with a pulse damper in which a flexible diaphragm is mounted at one side of a cavity through which the test liquid flows against one face of the diaphragm and the opposite face thereof has a coil spring imposed in a manner to resist the flexing of the diaphragm as pulsations from a pump discharge liquid thereagainst.

Several additional prior U.S. Pat. Nos. 4,163,461 to Jacobellis, dated Aug. 7, 1979, and 4,186,776 to Burton, dated Feb. 5, 1980, respectively show somewhat bulbous shaped cavities in which flexible diaphragms are disposed midway thereof for application of fluid pumped by a reciprocating pump against one face, while the portion of the cavity adjacent the opposite side of each diaphragm respectively contains gas under pressure, and a compressible fluid which appears to be gaseous as distinguished from a liquid.

There also is another type of pulse damper employed in systems for high pressure liquid chromatography, such as shown in prior U.S. Pat. No. 4,222,414, to Achener, dated Sept. 16, 1980, and in which a plastic spool made from material which is chemically inert with respect to fluids typically used in liquid chromatography is provided with an axial bore adequate in size to receive liquid delivered thereto upon each reciprocation stroke of the pump of the system, the spool preferably being formed from polytetrafluoro-ethylene, one type of which is sold under the trademark TEFLON. The spool is encased within a cylindrical housing which preferably is made from stainless steel and an annular chamber surrounds the spool and is filled with what is stated to be a compressible liquid but no specific type of compressible liquid is described.

In regard to the type of pulse damper disclosed in the above identified patent, it is known that an irremedial defect exists when used in high pressure chromatography systems in that, the bore size, and therefore the internal volume, must be predicated on the sensitivity, displacement per p.s.i., desired, and the resultant stress level. As the bore diameter tends to zero, the stress levels in the compliant tube approach infinity. For practical levels of stress, to avoid non-plastic deformation, the bore size for a practical device, and therefore the minimum internal volume, must be much greater than that necessary for mobile phase flow considerations.

The pulse damper comprising the present invention is a relatively simple device, highly effective in operation, and comprising distinct improvements over the prior art devices referred to hereinabove and details of which are set forth below.

SUMMARY OF THE INVENTION

It is among the principal objects of the invention to provide a simple pulse damper comprising a body in which a preferably cylindrical cavity extends thereinto from one face which preferably is planar and a diaphragm of limited flexibility and preferably formed of suitable plastic is clamped between said face of the body, and a cover having one face which is clamped against one face of the diaphragm, while the opposite face thereof is exposed to the cavity. The face of the cover adjacent the diaphragm has a groove of very limited cross-sectional dimension and preferably circular form therein and also preferably smaller in diameter than that of the cavity, and inlet and outlet ports also being formed in said cover and respectively communicating with said circular groove at diametrically opposite locations, the cavity being filled with a non-aqueous compressible liquid selected from the groups comprising alcohols and organo-salines. Of the first group, methanol is a highly desirable liquid and of the second group, a silicone is very effective.

Another object of the invention which is important is to provide a groove around the perimeter of the cavity in the planar face thereof and mount a circular self-energizing ring of material therein to form a shoulder-like fulcrum against which the diaphragm flexes in a manner to minimize fatigue of the diaphragm, which preferably is formed from TEFLON, which is polytetrafluoroethylene.

A still further object of the invention is to form the aforementioned groove in the cover adjacent the diaphragm in a circular configuration and of very limited cross-sectional dimension in order to flush the cavity on every stroke and thereby reduce the flushing volume drastically.

One other object of the invention is to facilitate forming an effective grip between one face of the diaphragm and the adjacent face of the cover which abuts it by forming in said face of the cover an annular groove of limited cross-sectional shape and, when clamped against the diaphragm, forces a limited amount of the diaphragm into said groove and thereby establishes an effective grip, as caused by a plurality of tightening bolts disposed in a circular pattern and extending through the body as well as the cover of the pulse damper.

One further object of the invention is to provide ports within the walls of the body which define the cavity and communicating therewith for purposes respectively of attaching a pressure gauge or conduits to a pressure gauge thereto and the other port serving as a filling opening.

Details of the foregoing objects and of the invention, as well as other objects thereof, are set forth in the following specification and illustrated in the accompanying drawings comprising a part thereof.

DETAILED DESCRIPTION OF THE PREFERRED EMBODIMENT OF THE INVENTION

Figure 1:
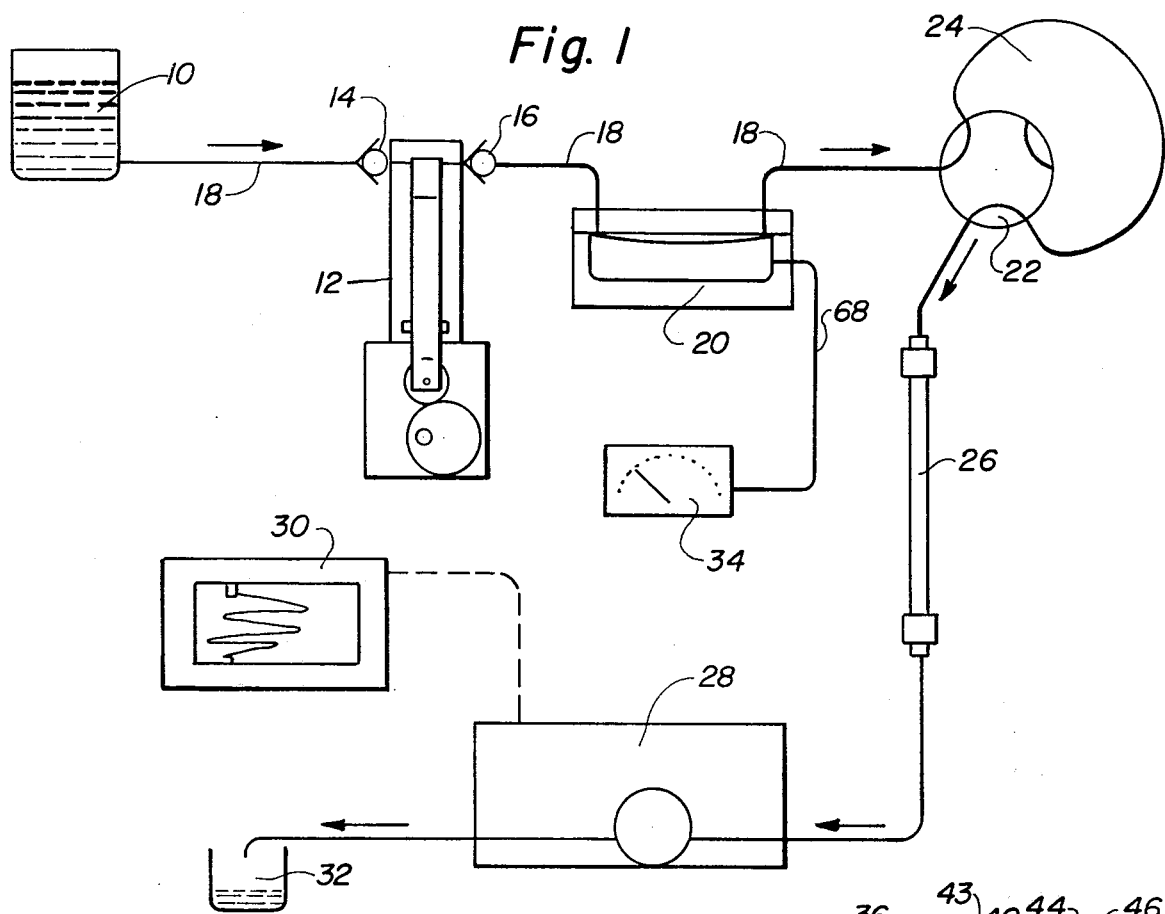
FIG. 1 is a diagrammatic view of a chromatography system which includes a pulse damper embodying the principles of the present invention.

For purposes of providing a relatively simple presentation of a system in which the pulse damper of the present invention is included, reference is made to FIG. 1 in which various elements of a typical system are illustrated. In practicing high pressure liquid chromatography, a mobile phase or liquid vehicle is supplied in a reservoir 10 and communicates with a reciprocating pump 12 having appropiate check valves 14 and 16. A conduit 18 connects the same and additional similar conduits lead the vehicle to and from a pulse damper 20 which embodies the invention. The conduit then communicates with an injection valve 22 mounted with respect to a storage supply 24 which contains the material to be analyzed and from which such material is sequentially injected into one end of the chromatography column 26 which is packed with appropriate material in accordance with chromatographic practice capable of separating the various components of the material to be analyzed and additional columns may be mounted in series with the one illustrated if required to analyze relatively complex material of many components.

In the operation of chromatographic systems, the liquid vehicle must not react chemically with the material to be analyzed and, correspondingly, neither the vehicle nor the material being analyzed are chemically reactive with the material with which the column 26 is packed. In modern, sophisticated chromatography systems, it may also include a detector 28 for the various components of the material being analyzed and the results may be automatically recorded for print-out or mechanism 30 and, after analysis, the material may be segregated, if desired, and/or discharged to waste means 32. Also, the pulse damper 20 is connected to a pressure sensor and indicator 34.

Figure 2A:
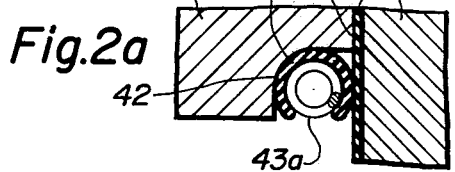
FIG. 2a is a cross-sectional view of a fragmentary detail.
Figures 2, 3, 4:
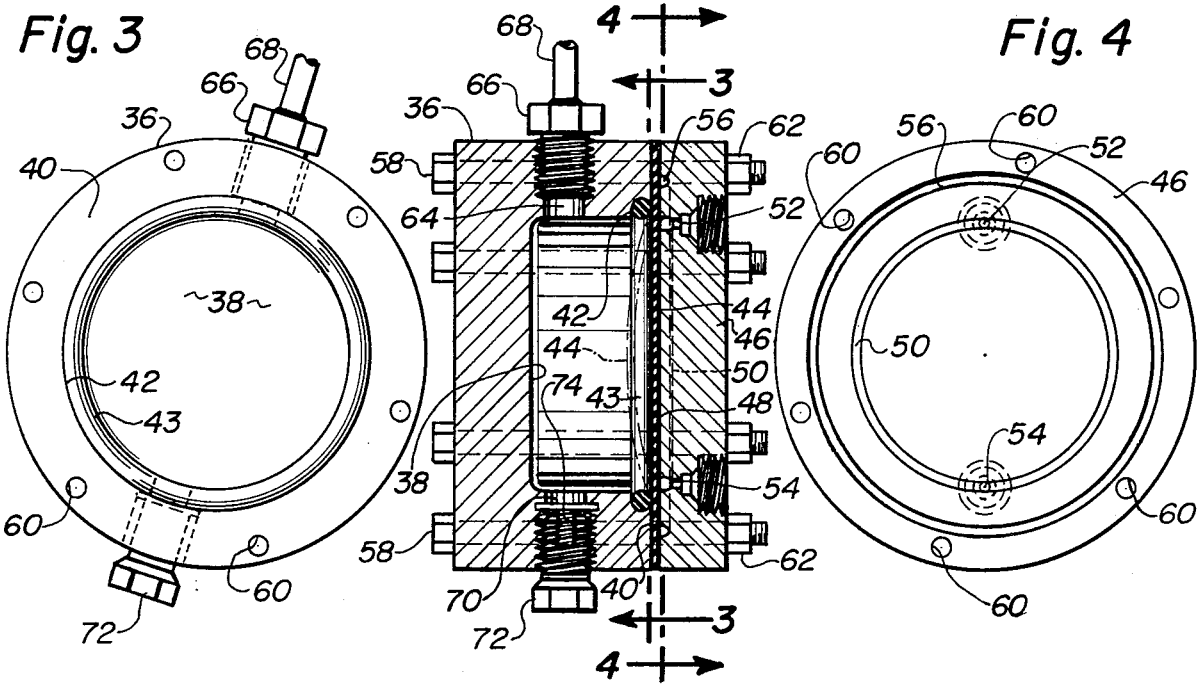
FIG. 2 is a vertical sectional view through the pulse damper which includes the present invention and illustrating the same in a slightly expanded manner.
FIG. 3 is a sectional view of the pulse damper of FIG. 2 as seen on the line 3—3 thereof and, FIG. 4 is a sectional view of the pulse damper shown in FIG. 2 as seen on the line 4—4 thereof.

Details of applicant's pulse damper are best illustrated in FIGS. 2–4 and are described as follows. A body 36 formed from suitable material and preferably metal, is illustrated as being cylindrical in shape as seen from FIGS. 3 and 4 but it is to be understood that other shapes may be used if desired. The body 36 is provided with a cavity 38 which also, especially for convenience of manufacture, may be cylindrical and formed by a boring tool. The open end of the cavity 38 preferably is within a flat plane 40 and the rim of the cavity 38 within the plane 40 is formed with a circular groove 42 comprising a seat which receives and supports a self-energizing seal 43 one form of which may comprise a molded circular member which is C-shaped in cross-section and of limited flexibility and contains a compressible coiled metallic spring 43a of suitable composition as shown in FIG. 2a. Member 43 preferably is formed from polytetrafluoro-ethylene, one type of which is sold under the trade name TEFLON.

Diaphragm 44 is formed of sheet plastic material of limited flexibility, also preferably TEFLON, but other suitable equivalent plastic materials may be used if not reactive chemically with material being processed. The diaphragm 44 extends across the flat face 40 of body 36 and preferably is commensurate in area with said face. The opposite face of diaphragm 44 is engaged by a cover 46 which is of material preferably similar to that from which the body 36 is formed and said cover has a planar face 48 in which a first circular groove 50 is formed. Cover 46 also is provided with a pair of similar, respectively inlet and outlet ports 52 and 54 which, as clearly shown in FIG. 4, intersect and communicate with the first circular groove 50.

As best shown in FIG. 2, the innermost ends of the ports 52 and 54 respectively are close to but nevertheless are slightly spaced radially inward from the sidewalls of the cavity 38 to provide desirable action of the diaphragm relative to circular member 43 and thereby minimize fatigue of the diaphragm incident to being flexed in response to the liquid vehicle from reservoir 10 and pump 12 being discharged through inlet port 52 for circulation around the circular ring 50 and then passed through outlet port 54 to the injection valve 22.

The circular shape of groove 50, as distinguished from a diametrically extending groove, is highly desirable to effect complete sweeping of the compressible liquid in cavity 38 so as to prevent stagnation of fluid in the flow path and also allow rapid solvent change or flow-through of gradient-proportioned solvents with minimum degradation. Further, the disposition of the circular groove 50 closely adjacent the rim of the cavity 38 but slightly radially inward therefrom, also contributes to the effective operation of the diaphragm upon the liquid in cavity 38 to damp the pulses imposed against the compressible liquid.

Further, for purposes of effecting a highly efficient grip between diaphragm 44 and the cover 46, the face 48 of the cover is provided with a second annular groove 56 which is adapted to be brought into tight clamping relationship against one face of the diaphragm 44 when, for example, the bolts 58, which extend through the circular pattern of holes 60 formed in both the body 40 and cover 46 are tightened by nuts 62 and threaded on the ends of the bolts and thereby force portions of diaphragm 44 into said groove 56 to increase the grip upon the diaphragm and prevent creeping thereof.

Body 36 also is provided with a port 64 into which a suitable head 66 may be threaded, the head 66 accommodating one end of conduit 68, as shown best in FIG. 1, which communicates with the pressure indicator 34. An additional port 70 also communicates with the interior of cavity 33 for purposes of serving as a filling opening and normally closed by plug 72. The plug 72 also has a small void 74 therein to contain a small defined amount of air during assembly, which may exit and be trapped in the compressible liquid in cavity 38.

The diaphragm 44, by extending across the ring 43, results in the ring acting as a seal between the diaphragm 44 and body 36, in addition to the ring acting as a resilient fulcrum over which the diaphragm flexes. The diaphragm 44 also protects ring 43 from contact with fluids being analyzed since such fluids engage only the opposite surface of the diaphragm 44 from that which engages the ring 43.

Without limitation thereto, but for purposes of affording at least some appreciation of practical sizes of pulse dampers embodying the invention, it has been found that when the damper is circular in shape, it is approximately three inches in diameter and has an overall thickness, including the cover 46, of approximately one and five-eighths inches. The cavity 38 has a diameter of approximately one and one-half inches and a comparable thickness to preferably hold approximately twenty ml. of compressible liquid such as methanol. Also, the body and cover preferably are made respectively from type 304 and 316 stainless steel. Further, the head 66 to which the pressure indicator gauge 34 is responsive, may be a pressure transducer and similarly may be made from type 17-4 Ph stainless steel.

Pulse dampers of the type to which the invention pertains have a diaphragm which is under very low stress. While high pressure liquid chromotgraphy operating pressures typically range from zero to 6000 p.s.i., the diaphragm of the type described above will exhibit more displacement under a vacuum of 14.7 PSID across it than occurs due to liquid compression at 6000 p.s.i. The support for the diaphragm and the structure is fully hydrostatic and frictionless, whereby the diaphragm automatically assumes the lowest stress accommodation to the displacement forced upon it. The pressures on both sides of the diaphragm essentially are identical, allowing the use of a pressure sensing device with chemical compatibility to the compressible liquid disposed in the cavity of the pulse damper. In contrast, diaphragm type pulse dampers using mechanical devices or solids to absorb the pulses have inherent limitations in regard to friction and uniform support to any stress in the diaphragm, resulting in inconsistent sensitivity and poorer diaphragm life. Further, the use of a substantially circular, peripheral type flow path, such as afforded by groove 50, assures complete sweeping of the cavity during each pulsation and avoids the possibility of only straight line flow between inlet and discharge ports.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

We claim:

1. A pulse damper for use with a reciprocating pump in a chromatography system to minimize the effect of the pulsations of liquid delivered to a chromatography column, said damper comprising in combination, a body having a cavity extending thereinto from one face thereof, a cover having a planar inner surface extending substantially across the entire extent thereof and connected tightly to the body to close said cavity, a flexible diaphragm which initially is parallel to said planar surface extending across the face of said cavity and overlying the edges thereof in a manner to be supported and clamped tightly thereover by said cover when affixed to said body, said cover having spaced fluid inlet and outlet ports extending therethrough adjacent opposite sides of said cavity and communicating with the face of said diaphragm which is opposite said cavity and respectively adapted to transmit fluid against said face of said diaphragm and remove it therefrom in a manner to subject said diaphragm to the surges of fluid from a reciprocating pump, and said cavity being filled with a non-aqueous compressible liquid, operable to damp said surges.

2. The pulse damper according to claim 1 in which the substantially planar face of said cover which is adjacent said diaphragm has a groove for fluid passage extending between and communicating with the inner ends of said inlet and outlet ports to transmit fluid therebetween and to apply fluid against said face of said diaphragm.

3. The pulse damper according to claim 2 in which said inlet and outlet ports of said cover are positioned closely to opposite sidewalls of said cavity to provide desirable flexing action of said diaphragm relative to the rim of the walls of said cavity.

4. The pulse damper according to claim 3 further including at the rim of said cavity an annular seat adjacent said diaphragm, and a self-energizing fulcrum and a seal member positioned within said groove and abutting said diaphragm in a manner to be responsive to flexing of said diaphragm and operable to minimize fatigue of said diaphragm and also effect sealing one face of the diaphragm to the body.

5. The pulse damper according to claim 2 in which said groove for fluid passage is substantially circular and said inlet and outlet ports intersect and communicate with said groove substantially at diametrically opposite positions thereon.

6. The pulse damper according to claim 1 in which said cavity is substantially circular and has sidewalls, the face of said body against which said cover is connected being substantially planar and of limited radially extending area against which one face of said diaphragm is clamped by said cover, said diaphragm being of substantially uniform thickness and formed of tough synthetic resin material of limited flexibility, and the face of said cover which abuts said diaphragm to clamp it has an endless groove of limited depth therein positionable against said diaphragm and operable to have a portion of the diaphragm deformed thereinto to enhance gripping of the diaphragm against creeping movement when flexed.

7. The pulse damper according to claim 1 in which the walls of the body defining said cavity have ports respectively in opposite walls connected respectively to a pressure sensor and a closure plug and through which said cavity may be filled with said compressible liquid.

* * * * *